US00PP13057P2

(12) United States Plant Patent
Bergman

(10) Patent No.: US PP13,057 P2
(45) Date of Patent: Oct. 8, 2002

(54) CHRYSANTHEMUM PLANT NAMED 'YOMANKATO'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/955,836

(22) Filed: Sep. 20, 2001

(51) Int. Cl.[7] ..... A01H 5/00
(52) U.S. Cl. ..... Plt./294
(58) Field of Search ..... Plt./294

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yomankato', characterized by its uniform and upright plant habit; strong and freely branching growth habit; dark green foliage; uniform and freely flowering habit; early flowering, eight-week response time; anemone-type inflorescences that are about 8.25 cm in diameter; pure white-colored ray florets with disc florets that are initially green, then with development, white with yellow apices; and good postproduction longevity with plants maintaining good substance and color for about three to four weeks in an interior environment.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yomankato'.

The new Chrysanthemum is a product of a planned breeding program conducted by the Inventor in Fort Myers, Fla. and Salinas, Calif. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in March, 1997, in Salinas, Calif., of a proprietary Chrysanthemum seedling selection identified as code number YB-3463, not patented, as the female, or seed, parent with the Chrysanthemum cultivar Yolafayette, disclosed in U.S. Plant Pat. No. 11,756, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity.

Asexual reproduction of the new Chrysanthemum by vegetative tip cuttings was first conducted in Fort Myers, Fla. in June, 1998. Asexual reproduction by cuttings has shown that the unique features of this new Chrysanthemum are stable and reproduced true to type in successive generations.

SUMMARY OF THE INVENTION

The cultivar Yomankato has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yomankato'. These characteristics in combination distinguish 'Yomankato' as a new and distinct Chrysanthemum:

1. Uniform and upright plant habit.
2. Strong and freely branching growth habit.
3. Dark green foliage.
4. Uniform and freely flowering habit.
5. Can be grown as a disbud or spray-type.
6. Early flowering, eight-week response time.
7. Anemone-type inflorescences that are about 8.25 cm in diameter.
8. Pure white-colored ray florets with disc florets that are initially green, then with development, white with yellow apices.
9. Good postproduction longevity with plants maintaining good substance and color for about three to four weeks in an interior environment.

Compared to plants of the female parent selection, plants of the new Chrysanthemum are more freely branching, are more compact and have smaller inflorescences.

Plants of the new Chrysanthemum differ primarily from plants of the male parent, the cultivar Yolafayette, in inflorescence type and ray floret coloration as plants of the new Chrysanthemum have anemone-type inflorescences with white ray florets whereas plants of the cultivar Yolafayette have daisy-type inflorescences with yellow ray florets. In addition, plants of the new Chrysanthemum have larger inflorescences than plants of the cultivar Yolafayette.

Plants of the new Chrysanthemum can be compared to plants of the cultivar Shasta, disclosed in U.S. Plant Pat. No. 9,314, a daisy-type Chrysanthemum. In side-by-side comparisons conducted by the Inventor in Salinas, Calif., plants of the new Chrysanthemum differed from plants of the cultivar Shasta in the following characteristics:

1. Plants of the new Chrysanthemum had stronger and darker green foliage than plants of the cultivar Shasta.
2. Plants of the new Chrysanthemum had larger inflorescences than plants of the cultivar Shasta.

Plants of the new Chrysanthemum can also be compared to plants of the cultivar White Blush, disclosed in U.S. Plant Pat. No 9,441, a daisy-type Chrysanthemum. In side-by-side comparisons conducted by the Inventor in Salinas, Calif., plants of the new Chrysanthemum differed from plants of the cultivar White Blush in the following characteristics:

1. Plants of the new Chrysanthemum had stronger, more durable, foliage than plants of the cultivar White Blush.
2. Plants of the new Chrysanthemum had smaller inflorescences than plants of the cultivar White Blush.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Yomankato' grown as a spray-type.

The photograph on the second sheet comprises a close-up view of typical inflorescences of 'Yomankato' grown as a spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of pinching, the photoinductive short day/long night treatments were started. Plants used for this description were grown as spray-types. Measurements and numerical values represent averages of typical flowering plants.

Botanical classification: *Chrysanthemum×morifolium* cultivar Yomankato.

Commercial classification: Anemone-type potted Chrysanthemum.

Parentage:

*Female, or seed, parent.*—Proprietary *Chrysanthemum×morifolium* seedling selection identified as code number YB-3463, not patented.

*Male, or pollen, parent.*—*Chrysanthemum×morifolium* cultivar Yolafayette, disclosed in U.S. Plant Pat. No. 11,756.

Propagation:

*Type.*—Terminal tip cuttings.

*Time to initiate roots.*—About four days at 21° C.

*Time to produce a rooted cutting .*—About ten days at 21° C.

*Root description.*—White, fibrous.

*Rooting habit.*—Freely branching.

Plant description:

*Appearance.*—Herbaceous anemone-type potted Chrysanthemum that can be grown as a disbud or as a spray-type. Stems mostly upright and somewhat outwardly spreading; uniform crown. Very freely branching, about five or six lateral branches develop after removal of terminal apex (pinching); dense and full plants.

*Plant height.*—About 29 cm.

*Plant width.*—About 43 cm.

*Lateral branches.*—Length: About 23.5 cm. Diameter: About 5 mm. Internode length: About 2.5 cm. Strength: Strong. Texture: Pubescent. Color: 146A.

*Foliage description.*—Arrangement: Alternate. Quantity of leaves per lateral stem: About 10 or 12. Length: About 7.8 cm. Width: About 5.1 cm. Apex: Cuspidate to mucronate. Base: Attenuate. Margin: Palmately lobed, sinuses between lateral lobes parallel to divergent. Texture: Upper and lower surfaces with very fine pubescence; veins prominent on lower surface. Color: Young foliage, upper surface: Darker than 147A. Young foliage, lower surface: Darker than 147B. Mature foliage, upper surface: Darker than 147A. Mature foliage, lower surface: Closest to 147B. Venation, upper surface: Close to 146B to 146C. Venation, lower surface: 147B to 146C. Petiole length: About 1.8 cm. Petiole diameter: About 3.5 mm. Petiole color, upper and lower surfaces: Close to 146B to 146C.

Inflorescence description:

*Appearance.*—Anemone-type inflorescence form with elongated oblong-shaped ray florets. Inflorescences borne on terminals above foliage. Disk and ray florets arranged acropetally on a capitulum. Not fragrant. Can be grown as a disbud or spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 46 to 51 days later when grown as a disbud-type and about 48 to 54 days later when grown as a spray-type.

*Postproduction longevity.*—Inflorescences maintain good color and substance for about three to four weeks in an interior environment.

*Quantity of inflorescences.*—About 10 inflorescences per lateral branch.

*Inflorescence bud.*—Height: About 5 mm. Diameter: About 7 mm. Color: Close to between 137A to 146A.

*Inflorescence size.*—Diameter: About 8.25 cm. Depth (height): About 1.7 cm. Diameter of disc: About 2.8 cm. Receptacle diameter: About 7 mm.

*Ray florets.*—Shape: Elongated-oblong; narrow. Orientation: Initially upright, then about 75 to 80° from vertical. Aspect: Flat to reflexed; straight. Length: About 4 cm. Width: About 8 mm. Apex: Acute or emarginate. Base: Attenuate; short corolla tube. Corolla tube length: About 4 mm. Margin: Entire. Texture: Smooth, glabrous, satiny. Number of ray florets per inflorescence: About 24 arranged in one row. Color: When opening and fully expanded, upper surface: Closest to 155D. When opening and fully expanded, lower surface: Closest to 155D.

*Disc florets*.—Arrangement: Massed at center of receptacle; enlarged. Shape: Tubular, elongated and flared at apex. Apex: Five-pointed. Length: About 1.7 cm. Width: Apex: About 5.5 mm. Base: About 2 mm. Number of disc florets per inflorescence: About 155. Color: Immature: Between 143A and 144A, then becoming 154A. Mature: Apex: Close to 3A. Midsection: Closest to 155D. Base: Closest to 150D.

*Peduncles*.—Length: First peduncle: About 5.9 cm. Fourth peduncle: About 10.5 cm. Seventh peduncle: About 12.1 cm. Diameter: About 3 mm. Angle to vertical: About 45° from vertical. Strength: Moderately strong, flexible. Texture: Pubescent. Color: 146A.

*Reproductive organs*.—Androecium: Present on disc florets only. Anther color: 9A. Pollen: Not observed. Gynoecium: Present on both ray and disc florets.

*Seed*.—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yomankato', as illustrated and described.

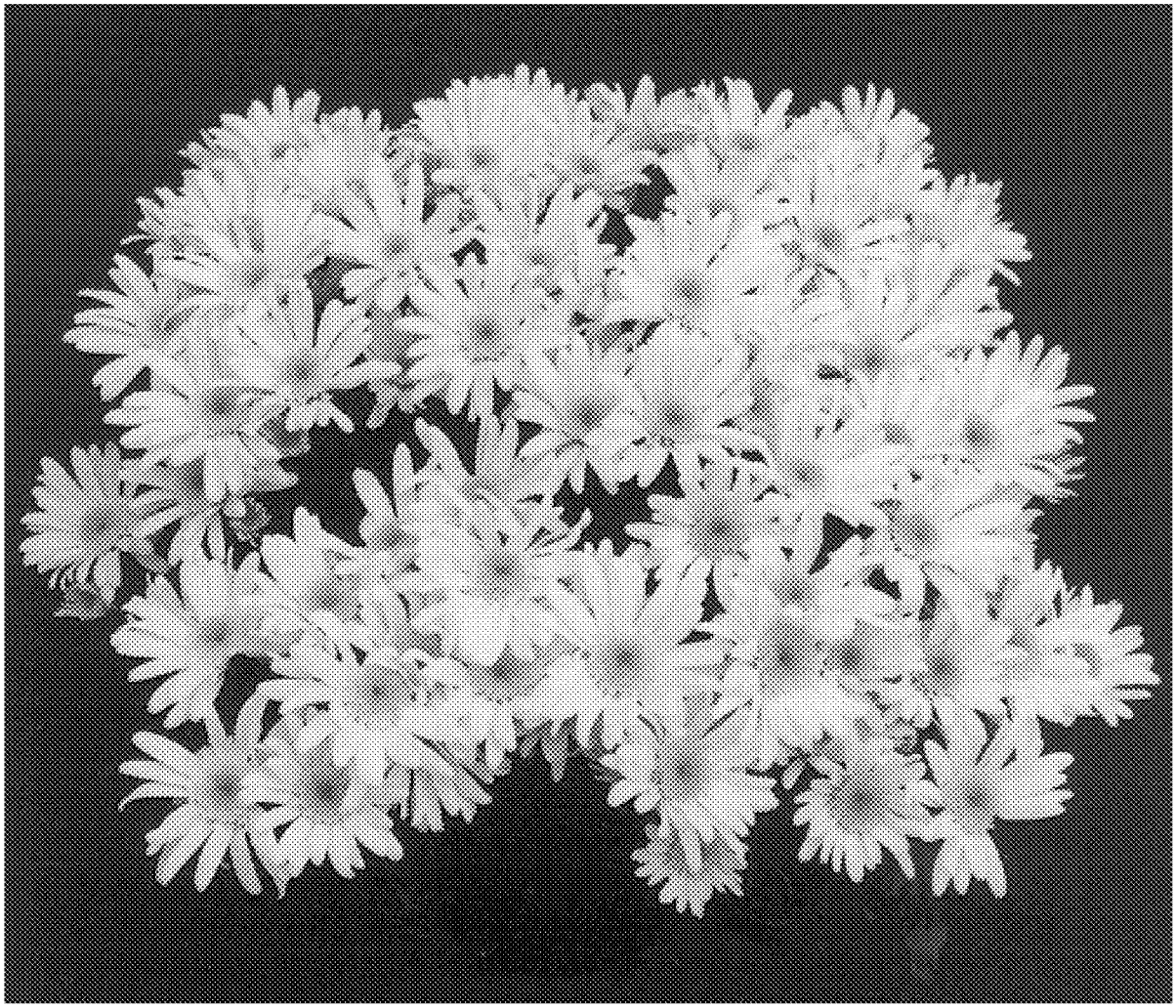

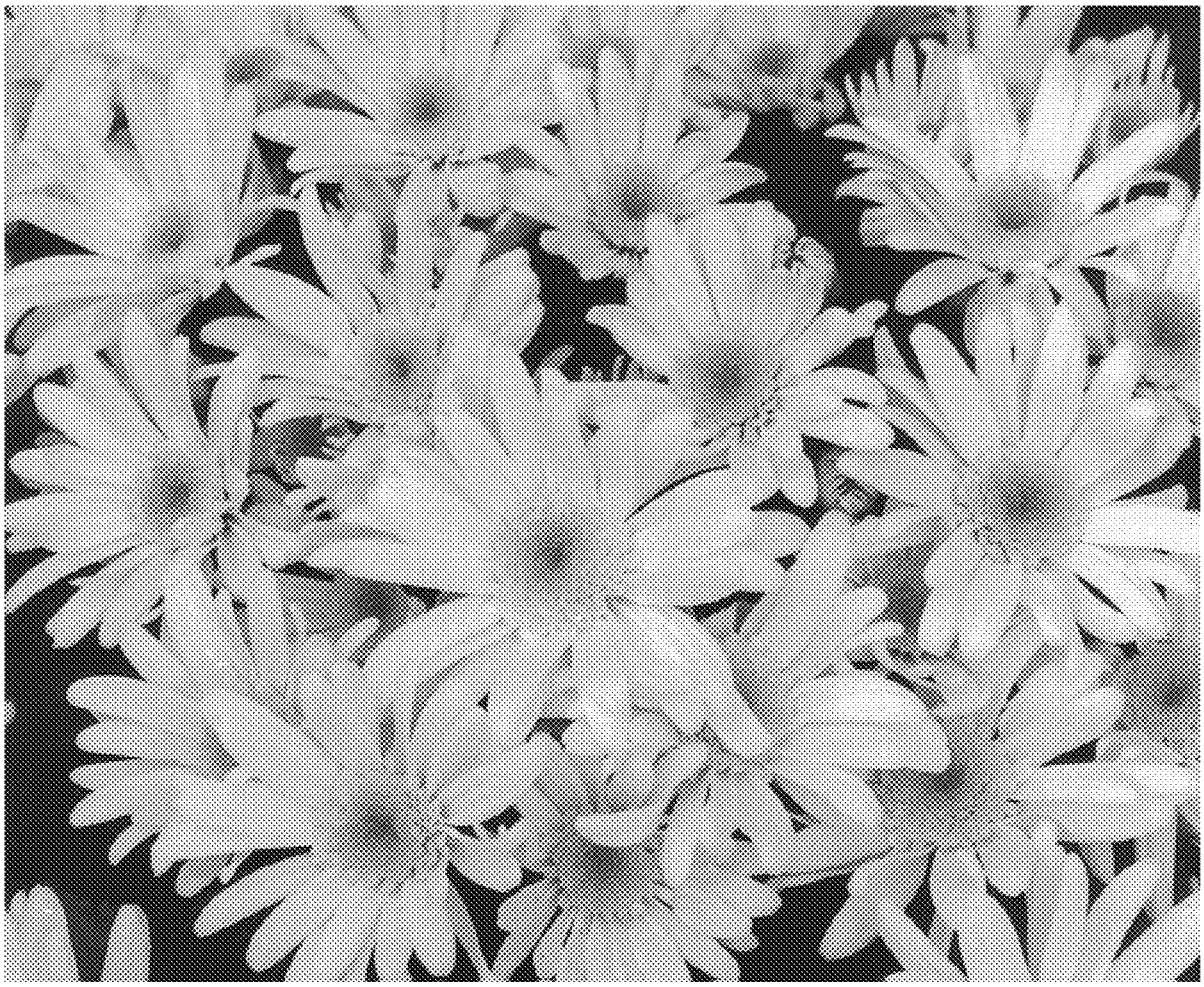

* * * * *